United States Patent [19]

Busnel et al.

[11] Patent Number: 5,024,852

[45] Date of Patent: Jun. 18, 1991

[54] PROCESS FOR PREPARING A PROPHYLACTIC DEVICE MADE OF RUPTURABLE MICROCAPSULES AND LAYERS OF ELASTOMERIC MATERIAL

[75] Inventors: René-Guy Busnel, Bievres; Gilles Argy, La Queue en Yvelines, both of France

[73] Assignee: Hutchinson, Paris, France

[21] Appl. No.: 500,377

[22] Filed: Mar. 28, 1990

Related U.S. Application Data

[62] Division of Ser. No. 232,336, Aug. 15, 1988, Pat. No. 4,930,522.

[30] Foreign Application Priority Data

Aug. 20, 1987 [FR] France ................................ 87 11753

[51] Int. Cl.$^5$ ................................................ A61K 9/50
[52] U.S. Cl. ........................................ 427/2; 2/161 R;
2/168; 128/844; 204/180.3; 427/203; 427/384;
427/412.1; 427/430.1; 604/292; 604/347
[58] Field of Search ............... 427/2, 203, 384, 412.1,
427/430.1; 128/844; 604/292, 347; 2/161 R,
167, 168, 169; 424/404, 405, 409; 204/180.3

[56] References Cited

U.S. PATENT DOCUMENTS

| 2,586,674 | 2/1952 | Lönne | 128/844 |
| 4,771,482 | 9/1988 | Shlenker | 2/168 |
| 4,853,978 | 8/1989 | Stockum | 604/292 |

Primary Examiner—Norman Morgenstern
Assistant Examiner—Terry J. Owens
Attorney, Agent, or Firm—Bell, Seltzer, Park & Gibson

[57] ABSTRACT

A process for the manufacture of a prophylactic device having contained therein at least one pharmaceutically active substance, comprising:
  forming a first layer of elastomeric material into the desired shape of the prophylactic device;
  prevulcanizing the first layer;
  applying to one side of the first layer a layer of microcapsules having at least one pharmaceutically active substance encapsulated therein;
  depositing on the coating of microcapsules a second layer of elastomeric material; and
  vulcanizing the first and second layers of elastomeric material. The device may be in the form of a contraceptive sheath, finger stall or glove, and protects the user from contamination by various germs, viruses, fungi and other pathogens in the whole area of the body covered by the device.

12 Claims, 1 Drawing Sheet

PROCESS FOR PREPARING A PROPHYLACTIC DEVICE MADE OF RUPTURABLE MICROCAPSULES AND LAYERS OF ELASTOMERIC MATERIAL

This application is a Divisional of application Ser. No. 232,336, filed Aug. 15, 1988 now U.S. Pat. No. 4,930,522.

FIELD OF THE INVENTION

The invention relates to prophylactic devices and processes for their manufacture.

In particular, it relates to prophylactic devices in the form of contraceptive sheaths suitable to help prevent contamination of their users by germs or viruses during sexual intercourse. It also relates to devices in the form of finger stalls or gloves that have protective effects for doctors and dentists who wear them during certain types of medical and dental examinations and surgery.

BACKGROUND OF THE INVENTION

In cases of medical or dental examination, surgery or sexual activity, the rupture or even cracking of the membrane such as rubber which forms the finger stall, glove or contraceptive sheath (condom) can result in contamination of both the person wearing the device and the partner; so their use has not been risk-free. The risk level for currently available contraceptive sheaths, measured by the value of the AQL factor (Acceptable Quality Level), is of the order of 0.4%, and is considered unsatisfactory by the medical profession as a whole. In an attempt to reduce the margin of risk, it has been proposed to associate a product active against the AIDS virus with contraceptive sheaths, the product being applied as a coating on the rubber forming the contraceptive sheath. Although this kind of device is theoretically satisfactory, it has disadvantages. For exmaple, the active product and the polymer comprising the sheath are capable of interacting to cause a modification of the elastic properties and aging properties of the sheath. In addition, the active product tends to become absorbed to and complexed with the rubber or other polymer forming the sheath and as a result, suffers a loss of pharmacological activity. Moreover, the repeated use of contraceptive sheaths having an active product applied in the form of a film to one or both sides thereof may lead to attack or irritation of the skin and/or mucosa of the sex partners, for example, by the active product, causing irritation, allergy, hypersensitivity, etc.

Devices consisting of an association of two separate latex sheaths with a pharmacologically active liquid disposed therebetween have been known for some time as described in U.S. Pat. No. 2,586,674. However, the active principles brought into direct contact with the latex or its derivatives act on the latter, very often rapidly destroying the mechanical properties, e.g., the impermeability, of the latex. Also, the liquid contained between the two sheaths tends to collect in one place when rubbing occurs, leaving much of the area of the organ covered with the sheath unprotected.

SUMMARY OF THE INVENTION

It is therefore an object of the present invention to provide a prophylactic device which mitigates the disadvantages associated with prior art devices.

It is another object of the present invention to provide a process for the manufacture of a prophylactic device.

These and other objects of the present invention are achieved by providing a prophylactic device comprising at least two layers of elastomeric material arranged one on top of the other, and microcapsules disposed between the two layers of elastomeric material, said microcapsules having rupturable walls and containing at least one pharmacologically active substance.

A process for the manufacture of a prophylactic device according to the present invention comprises forming a first layer of elastomeric material into the desired shape of the prophylactic device using an appropriate manufacturing technique; carrying out a prevulcanization treatment on the layer; applying to one side of the layer a film comprising microcapsules having one or more pharmacologically active substances enclosed therein; depositing on the film a second layer of elastomer also having the shape of the desired device; and vulcanizing the whole before removing it from the form.

In particular, in one embodiment, a fluidized bed of microcapsules containing the pharmacologically active substance(s) is placed on a first prevulcanized and preformed layer of elastomer such that the microcapsules adhere to the layer. The second layer of elastomer is then deposited on the microcapsules, followed by vulcanization of the whole.

In yet another embodiment of the present invention, the microcapsules are homogeneously dispersed in a latex of elastomer which is then deposited onto a first layer of prevulcanized, pre-formed elastomer, followed by vulcanization of the whole.

Prophylactic devices according to the present invention, when it contact with the skin and/or mucosa of the user, release the pharmacologically active product only when a layer of elastomer and the microcapsules rupture. Thus, the effects of habituation, and any destructive interactions between the elastomeric material and the active product are minimized.

BRIEF DESCRIPTION OF THE DRAWINGS

The invention will now be described by reference to the accompanying drawings, wherein.

DETAILED DESCRIPTION OF THE PREFERRED EMBODIMENT

Figure 1:
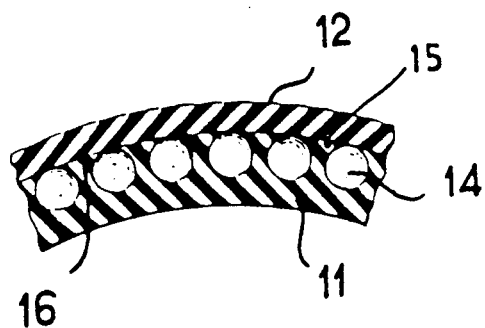
FIG. 1 is a schematic, sectional view of a first embodiment of the present invention.

FIG. 1 illustrates a first embodiment of a prophylactic device according to the present invention. Microcapsules 14 having rupturable walls which enclose therein at least one pharmacologically active substance are adhered to the outside 15 of a first elastomeric layer 12. A second elastomeric layer 11 is then applied thereto so as to coat the microcapsules and mechanically join to the first elastomeric layer in the spaces between the microcapsules by forming bridges 16 between the two layers. The term "pharmacologically active" is meant to include substances active against germs such as bacteria, viruses, fungi, spermatozoa, etc. By the term "rupturable", it is meant that the walls of the microcapsules rupture under the action of rubbing, shearing or wiping.

To manufacture a prophylactic device illustrated in FIG. 1, a first layer of elastomeric material 12 is deposited on a production form or mold of ceramic, glass or similar material which defines the form of a glove, finger stall or contraceptive sheath. The elastomeric layer, which may be comprised of natural rubber, can be obtained by immersion in a latex with capillary fixation under the action of coagulants, or advantageously by an electrophoretic process. The first layer is then subjected to a prevulcanization treatment in a hot air tunnel. The temperature in the tunnel and the passage time are set so that the elastomer will not be totally vulcanized and thus will retain the adhesive properties necessary for the microcapsules to adhere to the outside thereof. The microcapsules, having enclosed therein at least one pharmacologically active substance, are then deposited onto the outside of the elastomeric layer and remain fixed thereto by adhesion. In this embodiment, the microcapsules are applied to the elastomeric layer in the form of a fluidized bed of microcapsules. The whole is then coated with second elastomeric layer 11 preferably by immersing the whole in a bath of latex, wherein the elastomer coats the microcapsules and penetrates the spaces between the microcapsules and forms bridges 16 with layer 12 trapping microcapsules 14 therebetween and such that layers 11 and 12 become mechanically joined together. The product is then vulcanized by a second passage through a hot air tunnel at a temperature which is in all cases lower than that which is capable of damaging the pharmacologically active product and/or the walls of the microcapsules.

Microcapsules for use in the present invention may be prepared by a coacervation process or by other conventional methods known in the art of inclusion of pharmaceutical products and in the flexible substrate art, i.e., the carbonless copy paper art. The microcapsules or microspheres form a matrix system, the shell of which is made of a known material such as cellulose acetophthalate, polyvinyl alcohol, pectin, gum arabic, methyl cellulose, gelatin, epoxy resin or the like. The microcapsules are prepared so that the walls or shells will rupture when subjected to rubbing, shearing or wiping and thus release the active product(s) contained therein.

The pharmacologically active product can consist of one compound or a mixture of several chemically compatible compounds to produce a desired pharmacological effect, including but not limited to an anti-viral effect acting on the AIDS virus, herpes virus, etc., a spermicidal, fungicidal, trichomonacidal, bactericidal effect, or combination of any of the above ("all-embracing" effect). Representative examples of pharmacologically active substances useful in the present invention include the following: moroxydine hydrochloride, vidarabine, aciclovir, 5-iododeoxycytidine and idoxuridine (DCI); quaternary ammonium compounds such as alkyldimethylbenzylammonium chloride, benzalkonium chloride, hexylresorcinol of acid pH with added benzyldodecinium bromide, or of neutral pH with sodium laurylsulfate, nonoxyol, paradiisobutyl phenoxypolyethoxyethanol, benzethonium chloride (DCI) and phenyl-mercury nitrate with added methyl parahydroxybenzoate, miconazole nitrate, econazole nitrate, nystatin, nifuratel and natamycin, acetarsol, chlorquinaldol (5,7-dichloro-8-hydroxyquinaldine), tenonitrozole (DCI) and ternonidazole (DCI), iodinated polyvinylpyrrolidones, chlorhexidine (DCI), digluconate, neomycin sulfate (DCI) and polymyxin B sulfate (DCI); and sodium hypochlorite, potassium permanganate, silver nitrate and mercury derivatives. Pharmaceutical excipients and/or preservatives may also be encapsulated in the microcapsules.

The pharmacologically active product may be dissolved in a solvent, the vaporization point of which is above the normal vulcanization temperature of the elastomer used in the layers. Examples include silicon oil, ethylene glycol and any other chemically and pharmacologically compatible solvent. In the case of water-soluble pharmacologically active substances, it may be preferred to polymerize the elastomer in an oven under pressure because this will prevent microcapsules whose walls comprise gelatin from busting under the effect of the vapor pressure.

In a preferred embodiment according to the present invention, the microcapsules have a mean diameter in the order of from 5 to 50 microns. Each layer of the elastomeric material has a thickness of from 10 to 50 microns when the device is in the form of a contraceptive sheath, and a greater thickness, which can be as much as 300 to 500 microns, when the device is in the form of a finger stall or glove. These dimensions allow for dynamics of small amplitude (consisting of two or three movements of a man wearing the contraceptive sheath and in the case of finger stalls or gloves, a pressure of 300 to 500 grams which is identical to that exerted in a wiping action, for example) to cause the simultaneoous tearing of the thin inner layer of elastomer and the rupture of the microcapsules wherein the active substance completely coats the organ covered by the device.

The type of process described hereinabove, which involves the mechanical joiner of the first and second elastomeric layers by the "bridges" of elastomer in the spaces between the microcapsules, contributes to the overall mechanical behavior of the device, such as the act of placing the device over the penis, finger or hand of the individual, which during sexual activity and medical or dental examination or surgery, respectively, certain sufficient forces cause the microcapsules to rupture, and the active substance to be released into the space between the layers of elastomer.

Figure 2:
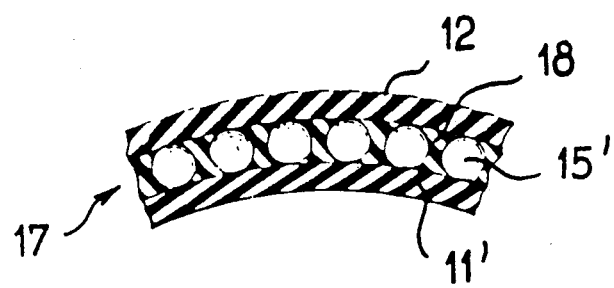
FIG. 2 is a schematic, sectional view of a second embodiment according to the present invention.

Turning now to FIG. 2 in which a second embodiment according to the present invention is illustrated, intermediate layer 17 contains microcapsules 15' in a matrix of elastomer 18 and is disposed between first elastomeric layer 12 and second elastomeric layer 11'. First elastomeric layer 12 is prepared in the same manner described above in reference to the embodiment illustrated in FIG. 1. After the prevulcanization step, however, the microcapsules are deposited onto the first elastomeric layer in the form of a homogeneous dispersion in an elastomeric latex. The second elastomeric layer is then deposited on the intermediate layer containing the microcapsules, followed by a vulcanization treatment of the whole. The elastomeric matrix 18 mechanically joins layer 12 to layer 11' analogously to the joinder of layer 12 to layer 11 in FIG. 1.

The embodiments illustrated in FIGS. 1 and 2 disclose a prophylactic device comprising two layers of mechanically joined elastomer having disposed therebetween rupturable microcapsules containing one or more pharmacologically active substances. However, it is self-evident that these embodiments can be modified to produce a multi-layer prophylactic device containing greater than two elastomeric layers, which exhibits increased mechanical strength and is capable of containing a greater quantity of active substances.

Figure 3:
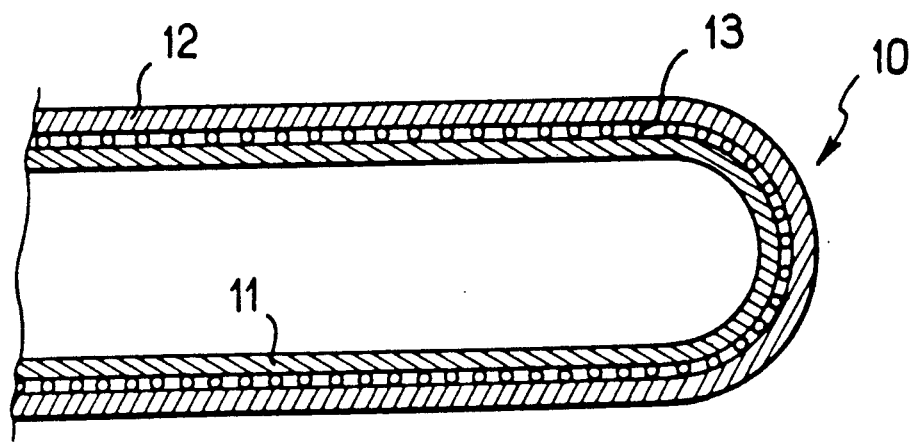
FIG. 3 is a schematic, sectional view of a prophylactic device according to the present invention.

Turning now to FIG. 3, prophylactic device 10 which may be a contraceptive sheath, a finger stall, surgical glove or the like, comprises two layers of elastomer 11 and 12, which may be based on natural rubber, between which microcapsules or microgranules containing one or more pharmacologically active product 13, are trapped.

The prophylactic devices according to the present invention exhibit increased mechanical strength and are capable of containing a variable amount of one or more pharmacologically active substances to protect the user thereof against contamination from many different pathogenic agents. The elastomeric layers comprising the devices are impermeable and release the pharmacologically active substance only when a constituent layer of elastomer and the microcapsules rupture. In addition, the layers are chemically compatible with the active substances and do not exhibit any adverse or destructive effects on them.

We claim:

1. A process for the manufacture of a prophylactic device having contained therein at least one pharmaceutically active substance, comprising:
   (a) forming a first layer of elastomeric material into the desired shape of the prophylactic device;
   (b) prevulcanizing the first layer;
   (c) applying to one side of the first layer a layer or microcapsules having at least one pharmaceutically active substance encapsulated therein;
   (d) depositing on the coating of microcapsules a second layer of elastomeric material; and
   (e) vulcanizing the first and second layers of elastomeric material.

2. A process according to claim 1, wherein said step of forming a first layer of elastomeric material comprises immersing a form defining the desired shape of the prophylactic device in a latex of the elastomeric material.

3. A process according to claim 2, wherein said first layer of elastomeric material is formed by capillary fixation in the presence of a coagulant.

4. A process according to claim 2, wherein said first layer of elastomeric material is formed electrophoretically.

5. A process according to claim 2, wherein said step of prevulcanizing said first layer is performed at a temperature and for a time such that the first layer of elastomeric material remains in a tacky state.

6. A process according to claim 5, wherein said step of applying a layer of microcapsules comprises positioning the first layer of elastomeric material in a fluidized bed of microcapsules while the first layer is in a tacky state so that the microcapsules adhere to the tacky surface of the first layer.

7. A process according to claim 1, wherein said step of depositing a second layer of elastomeric material comprises immersing the prevulcanized first layer of elastomeric material having the coating of microcapsules deposited thereon in a latex of the elastomeric material such that the elastomeric material coats the microcapsules and forms the second layer, contacting the first layer in spaces left between the microcapsules such that the microcapsules are traped therebetween.

8. A process according to claim 1, wherein said step of applying a layer of microcapsules comprises immersing the fist layer of elastomeric material in a latex of the elastomeric material containing a dispersion of the microcapsules such that an intermediate layer of elastomeric material having the microcapsules contained therein adheres to the first layer of elastomeric material.

9. A process according to claim 1, wherein said step of vulcanizing the first and second layers of elastomeric material is performed at a temperature low enough to avoid damage to the microcapsules and the at least one pharmaceutically active substance encapsulated therein.

10. A process according to claim 1, wherein the at least one pharmaceutically active substance is water-soluble, and is dissolved in a solvent having a vaporization point higher than the vulcanization point of the elastomeric material; and wherein said vulcanizing step comprises oven drying under pressure to avoid rupturing of the microcapsules due to the vapor pressure of the solvent.

11. A process for the manufacture of a multilaminar prophylactic device having contained therein at least one pharmaceutically active substance, comprising:
   (a) forming a first layer of elastomeric material into the desired shape of the prophylactic device;
   (b) prevulcanizing the first layer;
   (c) applying to one side of the first layer a coating o microcapsules having at least one pharmaceutically active substance encapsulated therein;
   (d) depositing on the thus applied coating of microcapsules a second layer of elastomeric material;
   (e) applying to the thus deposited second layer of elastomeric material another coating of said microcapsules;
   (f) depositing on the thus applied coating of microcapsules another layer of elastomeric material; and
   (g) vulcanizing the layers of elastomeric material;
   whereby a prophylactic device having two distinct layers of said microcapsules is produced.

12. A process according to claim 11, wherein the successive steps of applying another coating of microcapsules and depositing thereon another layer of elastomeric material are repeated at least once whereby a prophylactic device having at least three distinct layers of said microcapsules is formed.

* * * * *

UNITED STATES PATENT AND TRADEMARK OFFICE
CERTIFICATE OF CORRECTION

PATENT NO. : 5,024,852

DATED : June 18, 1991

INVENTOR(S) : René Guy Busnel, et al.

It is certified that error appears in the above-identified patent and that said Letters Patent is hereby corrected as shown below:

Column 1, lines 38 and 39 "exmaple" should be
-- example --.

Column 2, line 36, "it" should be -- in --.

Column 3, line 61, "nonoxyol" should be -- nonoxynol --.

Column 4, line 30, "simultaneoous" should be
-- simultaneous --.

Column 5, line 49, "claim 2" should be -- claim 1 --.

Column 6, line 11, "traped" should be -- trapped --.

Column 6, line 38, "o" should be -- of --.

Signed and Sealed this

Sixteenth Day of March, 1993

Attest:

STEPHEN G. KUNIN

*Attesting Officer*  *Acting Commissioner of Patents and Trademarks*